(12) United States Patent
Kimura et al.

(10) Patent No.: US 7,794,401 B2
(45) Date of Patent: Sep. 14, 2010

(54) ULTRASONIC PROBE FOR INTRA-CAVITY DIAGNOSIS AND MANUFACTURING METHOD THEREOF

(75) Inventors: Koichi Kimura, Kanagawa (JP); Toshizumi Tanaka, Saitama (JP)

(73) Assignees: Fujinon Corporation, Saitama (JP); FUJIFILM Corporation, Tokyo (JP)

( * ) Notice: Subject to any disclaimer, the term of this patent is extended or adjusted under 35 U.S.C. 154(b) by 652 days.

(21) Appl. No.: 11/299,766

(22) Filed: Dec. 13, 2005

(65) Prior Publication Data

US 2006/0184035 A1 Aug. 17, 2006

(30) Foreign Application Priority Data

Dec. 13, 2004 (JP) ............... 2004-360056

(51) Int. Cl.
*A61B 8/14* (2006.01)
(52) U.S. Cl. ............ 600/459; 600/437; 600/453; 310/334; 310/335; 310/336; 310/337; 310/317; 310/319; 310/322
(58) Field of Classification Search ............... 600/437, 600/459, 453; 310/334, 335–337, 317, 319, 310/322
See application file for complete search history.

(56) References Cited

U.S. PATENT DOCUMENTS

| 4,917,097 A | 4/1990 | Proudian et al. |
| 6,246,158 B1 | 6/2001 | Ladabaum |
| 2002/0087083 A1* | 7/2002 | Nix et al. .............. 600/459 |
| 2003/0004439 A1* | 1/2003 | Pant et al. .............. 601/2 |
| 2005/0146247 A1* | 7/2005 | Fisher et al. ............ 310/334 |

FOREIGN PATENT DOCUMENTS

| JP | 08-070496 A | 3/1996 |
| JP | 2000-139926 A | 5/2000 |
| JP | 2000-298119 A | 10/2000 |

OTHER PUBLICATIONS

Omer Oralkan, et al, "Volumetric Ultrasound Imaging Using 2-D CMUT Arrays", IEE E Transaction on Ultrasonic, Ferroelectrics, and Frequency Control, vol. 50, No. 11, Nov. 2003.
JP Notification of Reasons for Rejection, dated Apr. 14, 2010, issued in corresponding JP Application No. 2004-360056, 5 pages English and Japanese.

* cited by examiner

*Primary Examiner*—Brian Casler
*Assistant Examiner*—John F Ramirez
(74) *Attorney, Agent, or Firm*—Sughrue Mion, PLLC

(57) ABSTRACT

A diagnostic ultrasonic probe for use in body cavities has at its tip an ultrasonic transducer array, which has a layered structure wherein a flexible circuit board, an electric circuit, a backing material, a piezoelectric element array, an acoustic impedance matching layer and an acoustic lens are formed atop another on a supporting member. The electric circuit includes at least one of amplifiers for amplifying echo signals from ultrasonic transducers, switches for switching over between sending the echo signals from the ultrasonic transducers and receiving drive signals for exciting the ultrasonic transducers, a multiplexer for selective-switching between the echo signals as well as between the drive signals, an A/D converter for converting the echo signals from an analog form to a digital form, and a D/A converter for converting the drive signals from a digital form to an analog form.

15 Claims, 16 Drawing Sheets

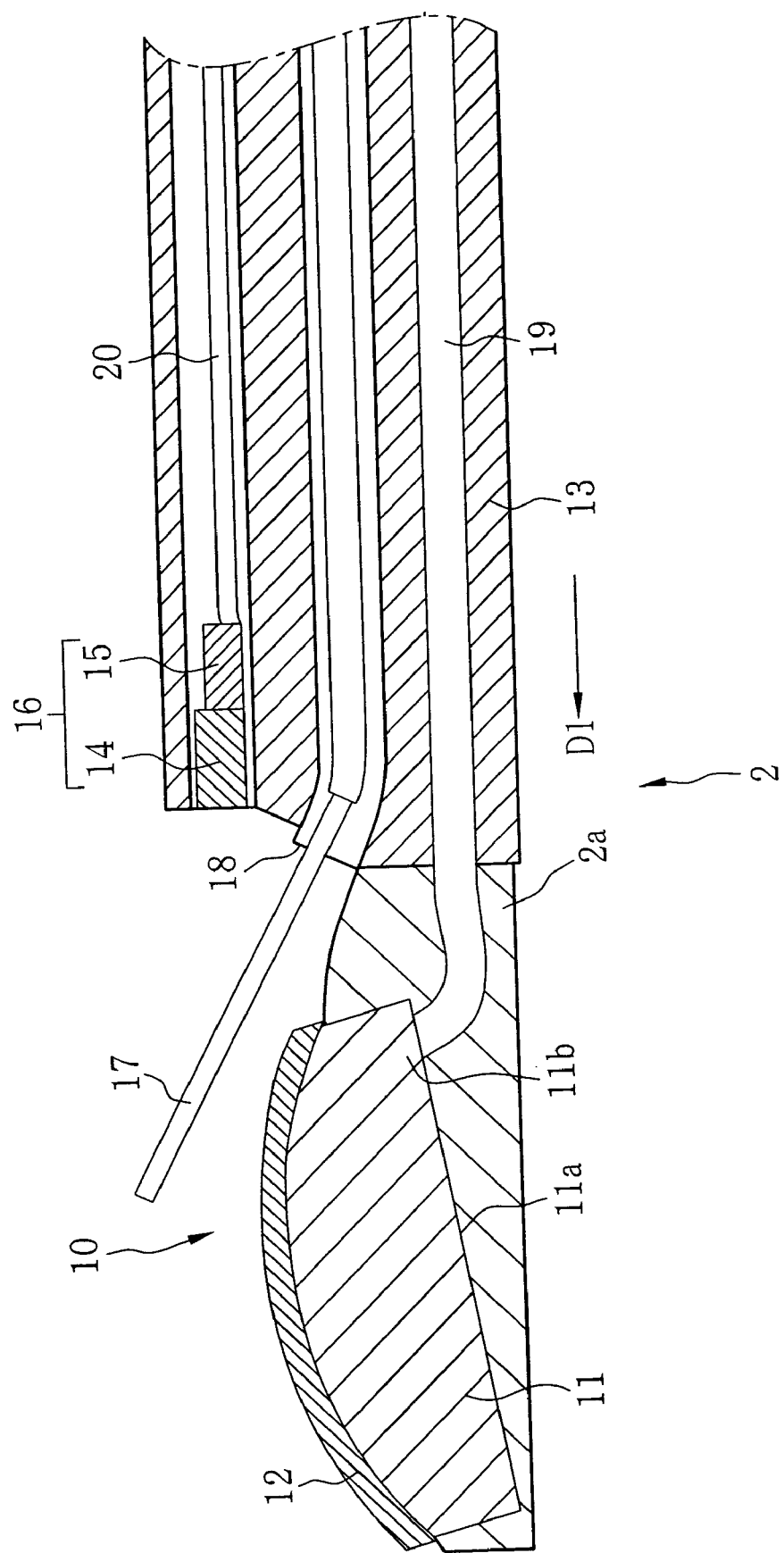

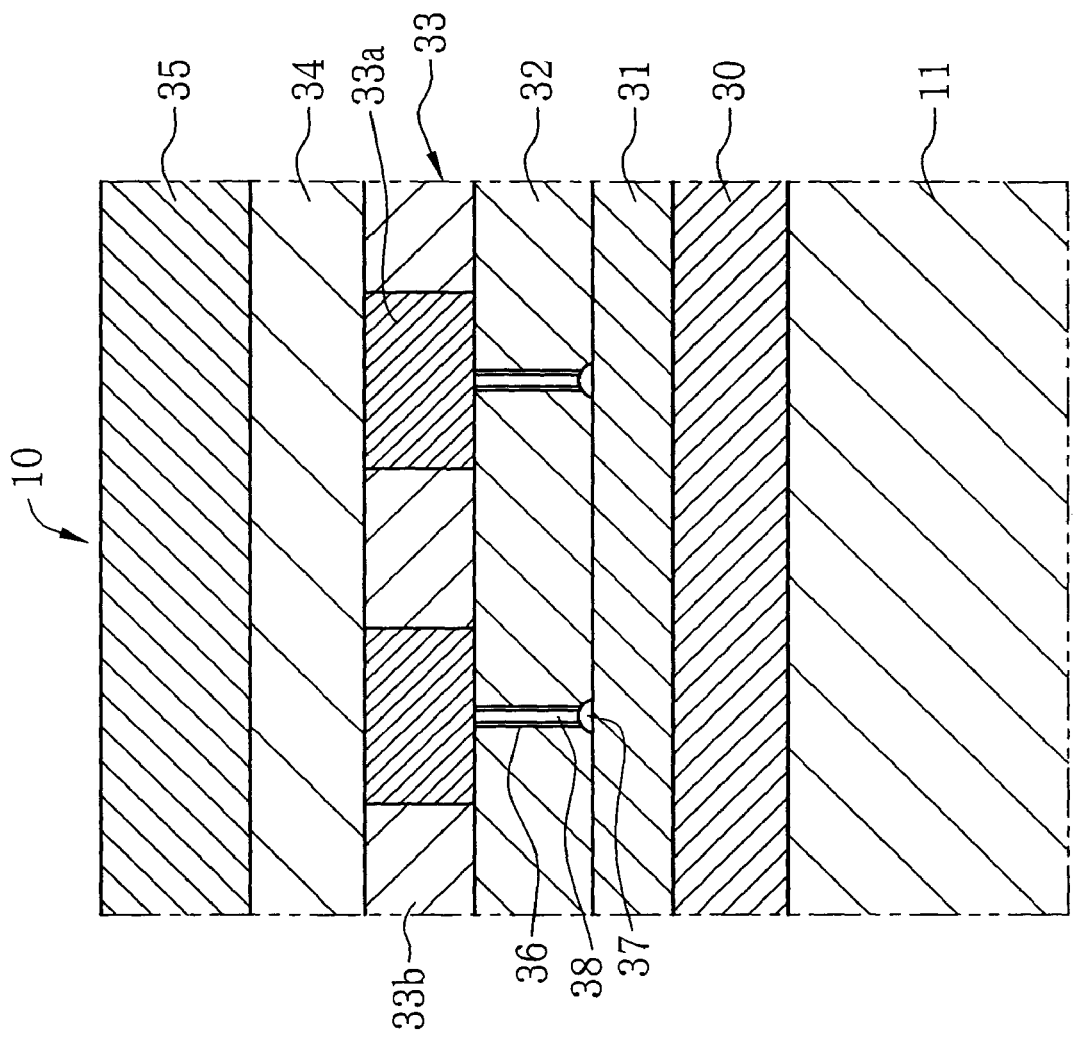

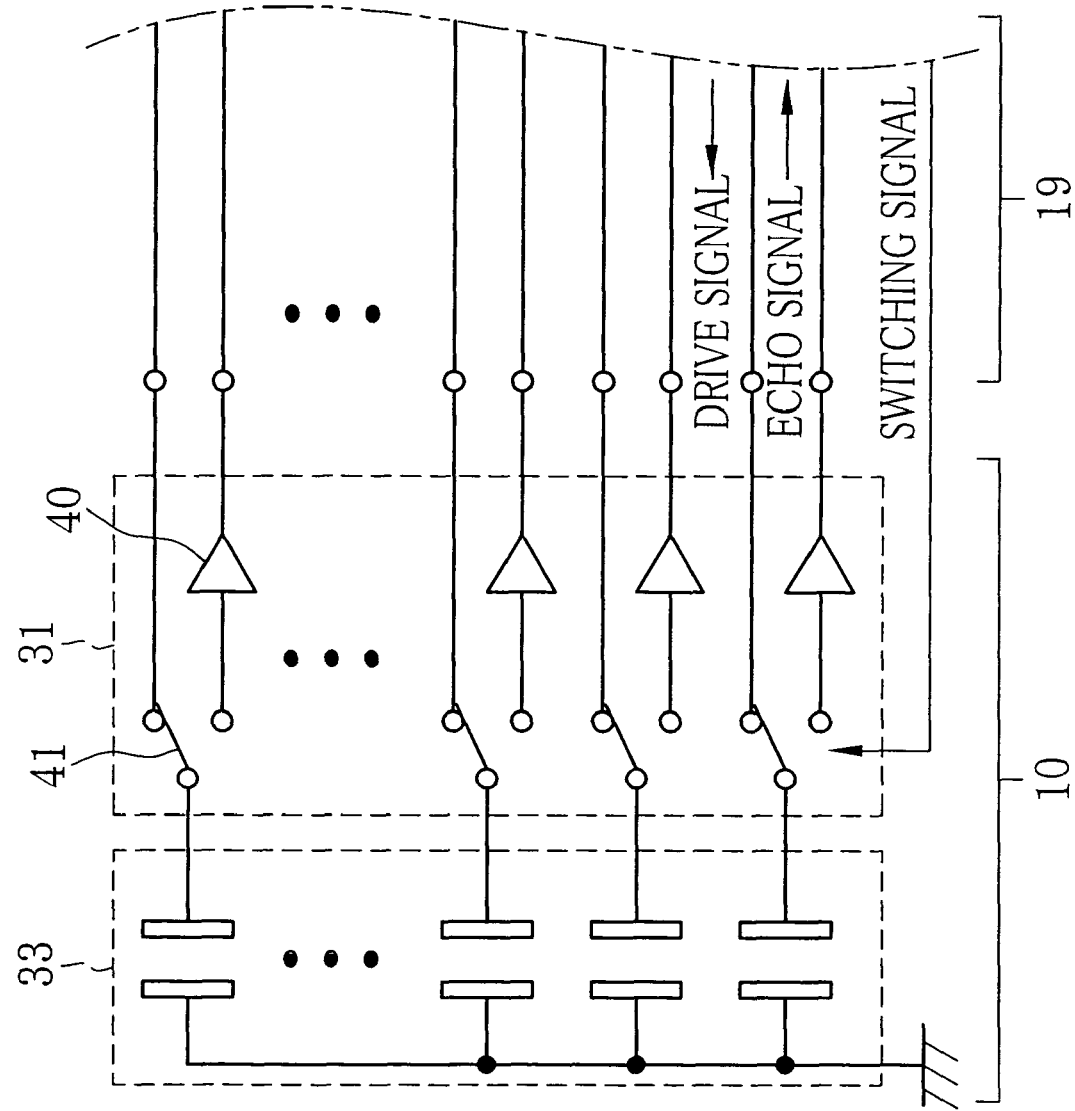

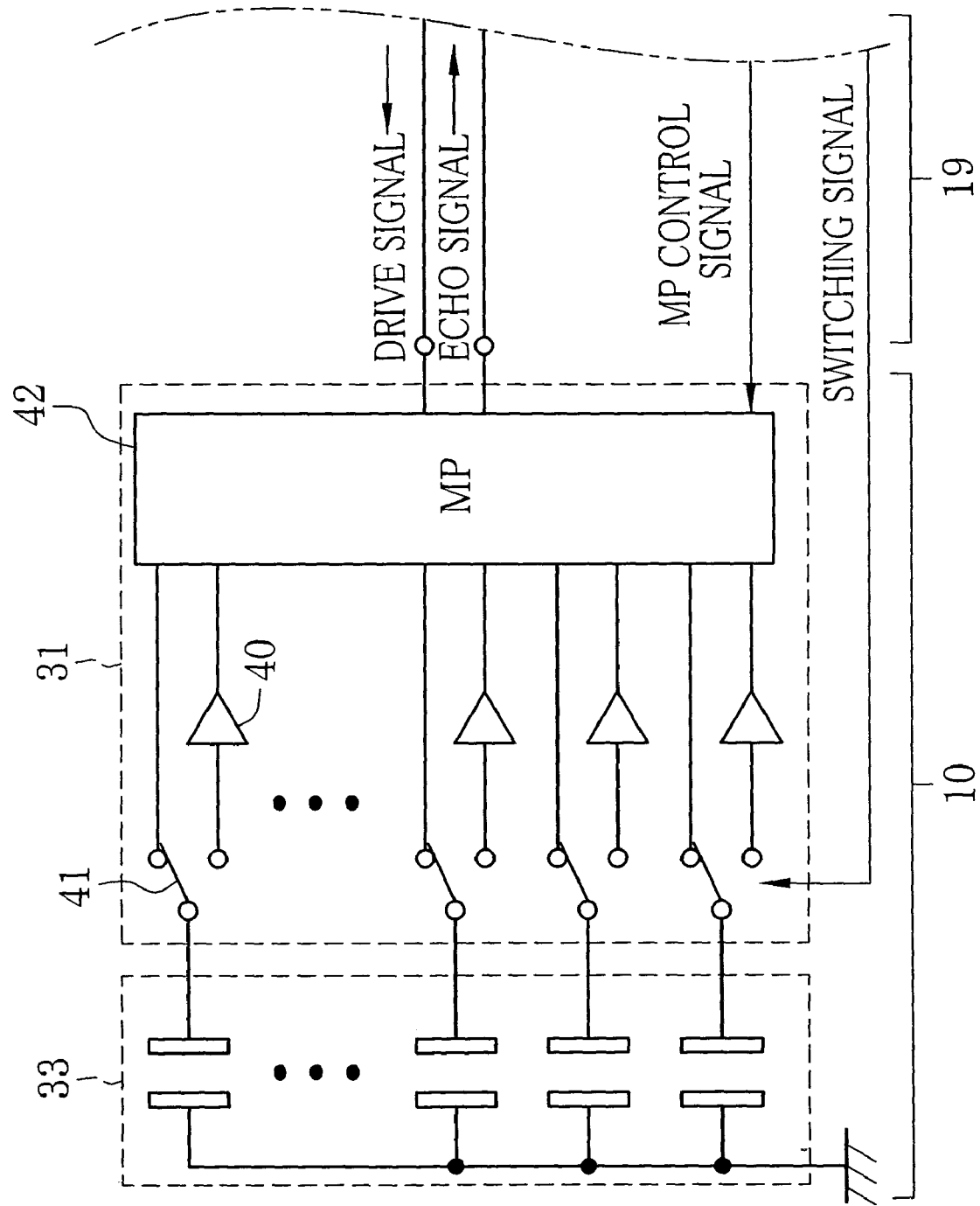

ULTRASONIC PROBE FOR INTRA-CAVITY DIAGNOSIS AND MANUFACTURING METHOD THEREOF

FIELD OF THE INVENTION

The present invention relates to an ultrasonic probe for intra-cavity diagnosis having an ultrasonic transducer array, which is inserted into body cavities to emit ultrasonic waves toward a necessary internal body part and receive echo signals from the body part, and a manufacturing method of the ultrasonic probe.

BACKGROUND ARTS

Medical diagnosis that utilizes ultrasound imaging has recently been widely used in medical fields. The ultrasonic image is obtained by emitting ultrasound from an ultrasonic probe toward a necessary body part and detecting echo from the body part as electric echo signals by use of an ultrasound observing device that is connected to the ultrasonic probe through a connector. The ultrasonic probes may be classified roughly into an intra-cavity diagnostic type that is inserted in a body cavity, and an extra-cavity diagnostic type that is moved on the body surface. As a known driving methods for the intra-cavity diagnostic ultrasonic probe, there is an electronic scanning method, wherein a plurality of ultrasonic transducers are selectively driven to send and receive the ultrasound, while being switched over by electronic switches or the like.

The electronic scanning type ultrasonic probes may be classified into a convex electronic scanning type and a radial electronic scanning type. In the convex electronic scanning type, the ultrasonic transducers, e.g. 94 to 128 transducers, are arranged on a semi-cylindrical surface of a probe tip. In the radial electronic scanning type, the ultrasonic transducers, e.g. 360, are arranged around a periphery of a probe tip.

In those types of ultrasonic probes using a plurality of ultrasonic transducers, such as the convex electronic scanning type and the radial electronic scanning type, it is necessary to provide wiring cables for sending and receiving many kinds of signals, including drive signals for exciting the individual transducers and the echo signals, between the ultrasound observing device and an electric circuit disposed in the ultrasonic probe. Therefore, the cables take up a certain thickness in the ultrasonic probe, and hinder making the ultrasonic probe finer, although it is desirable to make the intra-cavity type probe as fine as possible in order to ease the pain of the patient.

Since the available number of ultrasonic transducers to one probe is limited by the permissible thickness of the wiring cable, the resolving power of the ultrasonic image has also been limited. Beside that, if the wiring cable has a large capacitance, the echo signal will damp. Mismatching of electric impedance will lower the S/N ratio, and may also cause cross-talk between the wires, which can result in malfunction.

To solve the above problems, U.S. Pat. No. 4,917,097 suggests an ultrasonic transducer device wherein ultrasonic transducers are integrated with amplifies for the echo signals without using a wiring cable, and Japanese Laid-open Patent Application No. 2000-298119 suggests an ultrasonic transducer device wherein an electric circuit is mounted on a silicon substrate that is integrated with ultrasonic transducers made of composite piezoelectric elements, so as to make the wiring cables unnecessary for connecting the electric circuit and the ultrasonic transducers.

Recently, an ultrasonic transducer device using capacitive micromachined ultrasonic transducers, which utilize micro electromechanical system (MEMS), has been suggested, for example, in U.S. Pat. No. 6,246,158 and Oralken et al, "Volmetric Ultrasound Imaging Using 2-D CMUT Arrays", November 2003, IEEE TRANSACTION ON ULTRASONIC, FERROELECTRICS, AND FREQUENCY CONTROL, VOL. 50, NO. 11.

However, according to the prior arts disclosed in the above first and second materials, the amplifiers and the electric circuit are arranged in a lateral direction of the ultrasonic transducer. In that case, if the ultrasonic transducers are arranged to set their lateral direction in alignment with an inserting direction of the ultrasonic probe, the ultrasonic probe will have a relatively large hard portion including the ultrasonic transducers, increasing the load on the patient that may be caused by inserting the ultrasonic probe into the living body.

Furthermore, since the first and second prior arts refer to an example where the ultrasonic transducers are arranged in a linear array, if the amplifiers and the electric circuit are arranged laterally to the ultrasonic transducers, the wiring between these elements and the ultrasonic transducers will be complicated.

On the other hand, in the ultrasonic transducer device of the first prior art, U.S. Pat. No. 6,246,158, an electric circuit is disposed as a layer under the ultrasonic transducers. However, there is no concrete description about how to connect the electric circuit to wiring cables, how to arrange the ultrasonic transducers or how many ultrasonic transducers are available. Among all, there are not any suitable embodiments for the convex electronic scanning type or the radial electronic scanning type.

SUMMARY OF THE INVENTION

In view of the foregoing, a primary object of the present invention is to provide a diagnostic ultrasonic probe for use in body cavities, which permits making the probe tip finer, and lessen the above mentioned problems caused by the use of the wiring cable.

Another object of the present invention is to provide a method of manufacturing the inventive diagnostic ultrasonic probe for use in body cavities.

To achieve the above and other objects, an ultrasonic probe for intra-cavity diagnosis of the present invention comprises an ultrasonic transducer array disposed at a tip of the probe, the ultrasonic transducer array comprising a plurality of ultrasonic transducers arranged in an array, and an electric circuit including at least some of necessary electric elements for activating the ultrasonic transducers, the electric circuit being formed as a layer laid under the ultrasonic transducers.

The ultrasonic transducers may be piezoelectric elements. In that case, the ultrasonic transducer array preferably has a layered structure having at least a flexible substrate, the electric circuit, a backing material, an array of the piezoelectric elements and an acoustic impedance matching layer, which are formed atop another on a rigid supporting member, wherein the electric circuit and the piezoelectric elements are connected electrically through wires which are disposed in the backing material. The flexible substrate is preferably a circuit board having a circuit pattern formed thereon.

The ultrasonic transducer may also be capacitive micromachined ultrasonic transducers. In that case, the ultrasonic transducer array has a layered structure having at least a flexible substrate, the electric circuit and an array of the capacitive micromachined ultrasonic transducers, which are formed atop another on a rigid supporting member. It is more preferable to provide a backing material between the supporting member and the flexible substrate. The supporting member preferably has an ultrasound absorbing function. The flexible substrate is a circuit board having a circuit pattern formed thereon.

The electric circuit comprises at least one of amplifiers for amplifying echo signals from the ultrasonic transducers, switches for switching over between sending the echo signals from the ultrasonic transducers and receiving drive signals for exciting the ultrasonic transducers, a multiplexer for selective-switching between the echo signals and/or between the drive signals, an A/D converter for analog-to-digital conversion of the echo signals, and a D/A converter for digital-to-analog conversion of the drive signals.

According to a preferred embodiment, a wiring cable is provided for connecting the electric circuit to an ultrasound observing device that generates drive signals for exiting the ultrasonic transducers and produces ultrasound images from echo signals received from the ultrasonic transducers, the wiring cable being connected to a terminal that is provided at an end portion of a flexible substrate that is electrically connected to the electric circuit.

Forming the electric circuit, including at least some of necessary electric elements for the ultrasonic probe, as a layer under the ultrasonic transducers permits reducing the thickness or size of a hard portion, including the ultrasonic transducers, so the load on the patient is relieved.

Including the amplifiers in the electric circuit prevents the echo signals from suffering damping that is caused by transmission loss in the wiring cable or from noise interference. So the S/N ratio of the echo signal is improved. Including the multiplexer in the electric circuit permits reducing the requisite number of signal lines for the drive signals and the echo signals to merely two, so it is possible to reduce the diameter of the wiring cable. Including the A/D converter in the electric circuit permits sending the echo signals as digital signals through the wiring cable, so the echo signals will not damp in the wiring cable. Including the D/A converter in the electric circuit permits sending the drive signals as digital signals through the wiring cable, so the drive signals will not damp in the wiring cable.

As for the convex electronic scanning type ultrasonic probe, the wiring cable may be introduced at a base end portion of a supporting member on which the ultrasonic transducer array is mounted. In that case, it is preferable to incline the ultrasonic transducer array to an introducing direction of the wiring cable from the ultrasound observing device, such that the base end portion of the supporting material faces the wiring cable. This configuration facilitates introducing and connecting the wiring cable to the electric circuit.

A method of manufacturing an ultrasonic probe for intra-cavity diagnosis comprising an ultrasonic transducer array disposed at a tip of the probe, the ultrasonic transducer array comprising a plurality of ultrasonic transducers arranged in an array, the method comprising steps of:

forming an electric circuit on a silicon substrate, the electric circuit including at least some of electric elements for activating the ultrasonic transducers;

forming the ultrasonic transducers as a layer on the electric circuit as formed on the silicon substrate;

removing the silicon substrate while leaving the electric circuit; and affixing a flexible substrate to a back side of the electric circuit after the silicon substrate is removed.

The silicon substrate is preferably an SOI substrate where an insulator layer is sandwiched between two silicon layers, and the electric circuit is formed in an upper one of the two silicon layers, and a lower one of the two silicon layers is removed off the insulator layer after the ultrasonic transducers are formed on the electric circuit.

The capacitive micromachined ultrasonic transducers are superior to the piezoelectric elements, because the capacitive transducer can be formed integrally on an electric circuit, so the wires can be arranged more smartly as compared to a case using the piezoelectric elements. The capacitive transducer has a wider ultrasonic frequency band than the piezoelectric element, so that it can send and receive the ultrasonic waves of a wider variety of frequencies, enabling ultrasonic diagnosis in a deeper range of the living body. Besides that, the capacitive transducer generates less heat energy than the piezoelectric element, and is superior in efficiency of heat radiation to circumstances, as it can be formed directly on a silicon substrate. Therefore, the capacitive transducer is effective to suppress heat generation, which is one of the most important subjects of the ultrasonic probe for intra-cavity diagnosis.

BRIEF DESCRIPTION OF THE DRAWINGS

The above and other objects and advantages will be more apparent from the following detailed description of the preferred embodiments when read in connection with the accompanied drawings, wherein like reference numerals designate like or corresponding parts throughout the several views, and wherein:

FIG. 1 is an enlarged sectional view of a tip of an ultrasonic probe according to an embodiment of the present invention;

FIG. 3 is an enlarged sectional view of an ultrasonic transducer array using piezoelectric elements;

FIG. 4 is a circuit diagram illustrating an embodiment wherein amplifiers and switches are included in an electric circuit;

FIG. 5 is a circuit diagram illustrating another embodiment wherein amplifiers, switches and a multiplexer are included in an electric circuit;

FIG. 10A is a partially magnified sectional view of the tip of the ultrasonic probe shown in FIG. 10;

DESCRIPTION OF THE PREFERRED EMBODIMENTS

Figure 2A:
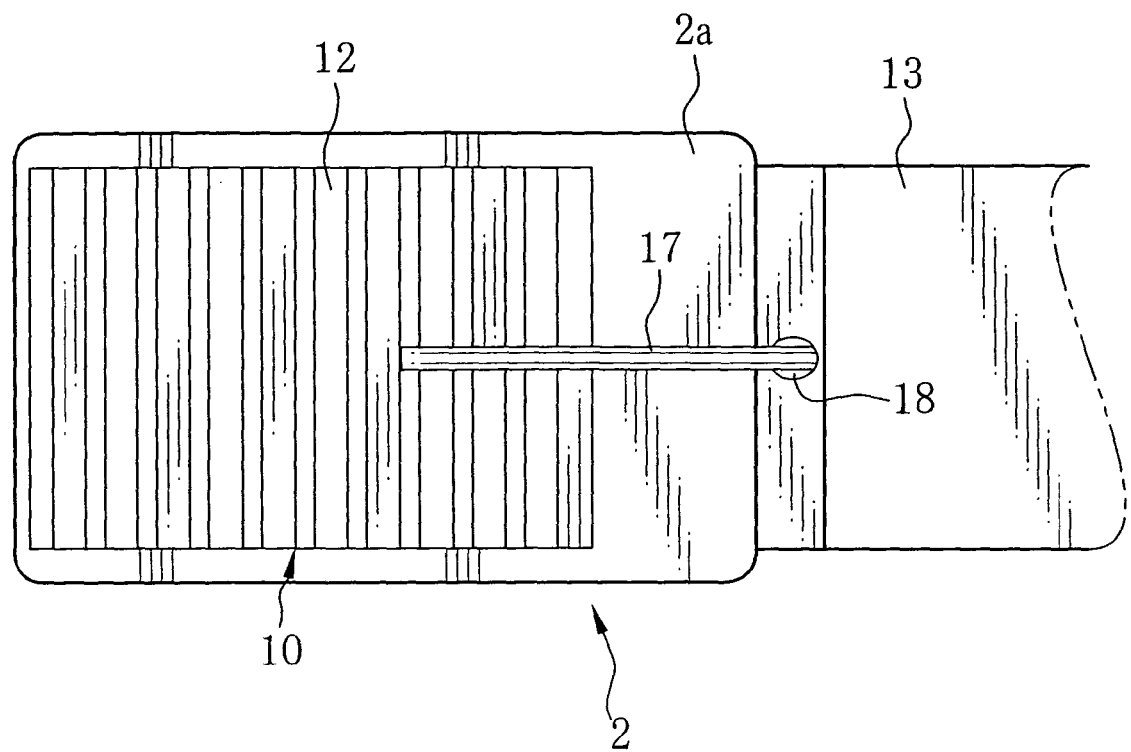
FIG. 2A is a top plan view of a linear ultrasonic transducer array.
Figure 2B:
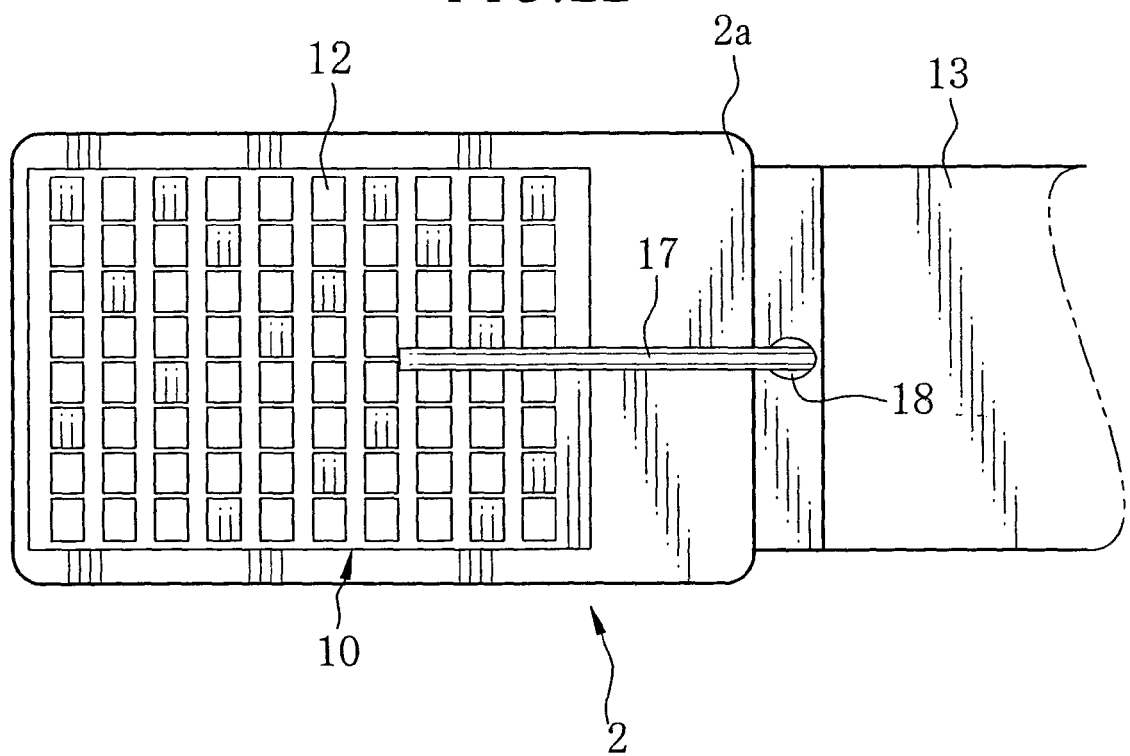
FIG. 2B is a top plan view of a two-dimensional ultrasonic transducer array.

As shown in FIG. 1, a body cavity diagnostic ultrasonic probe, hereinafter called simply the ultrasonic probe 2, has an ultrasonic transducer array 10 at its tip 2a. The ultrasonic transducer array 10 has an external diameter of about 5 mm to 8 mm, and is of a convex type which is constituted of a number of ultrasonic transducers 12 arranged in an array on a semi-cylindrical supporting member 11. The ultrasonic transducers 12 are arranged in a linear array as shown in FIG. 2A or in a two-dimensional array as shown in FIG. 2B.

The ultrasonic transducer array 10 is connected to a sheath 13 that has an external diameter of about 7 mm to 10 mm. An imaging device 16 is mounted in an upper portion of the sheath 13. The imaging device 16 is provided with an objective optical system 14 for forming an optical image of an internal body part to investigate, and a CCD 15 for capturing the optical image as an image signal. A channel 18 for putting a piercing needle 17 through it is formed through a center portion 18 of the sheath 13. On opposite sides of the piercing needle channel 18, an array wiring cable 19 and an imaging device wiring cable 20 are conducted through a lower portion of the sheath 13, so as to connect a not-shown ultrasound observing device and the ultrasonic transducer array 10 to the imaging device 16.

The supporting member 11 is made of a rigid material such as stainless steel. The ultrasonic transducer array 10 is inclined to an introducing direction D1 of the array wiring cable 19 from the ultrasound observing device through the sheath 13, so as to face a base end 11b of a back side 11a of the supporting material 11 to the array wiring cable 19. At the base end portion 11b of the supporting member 11, the array wiring cable 19 is inserted into the supporting member 11. A not-shown through-hole is formed through the supporting member 11, to conduct the array wiring cable 19 through it, and permit electric connection of the array wiring cable 19 to a flexible circuit board 30 and an electric circuit 31, as will be described with reference to FIG. 3.

In an embodiment shown in FIG. 3, the ultrasonic transducer array 10 has a layered structure wherein the flexible circuit board 30 of 50 μm to 1 mm thick, the electric circuit 31, a backing material 32, a piezoelectric element array 33, an acoustic impedance matching layer 34 and an acoustic lens 35 are formed atop another on the supporting member 11. The electric circuit 31 usually consists of a single or a number of semiconductor chips, and the acoustic lens 35 is 0.5 mm to 11.0 mm thick and has a radius of curvature of 5 mm to 10 mm. The flexible substrate 30 is provided with a not-shown circuit pattern, and is connected electrically to the electric circuit 31. Although it is not shown in detail, the flexible substrate 30 and the electric circuit 31 are electrically connected to the array wiring cable 19 that is inserted into the supporting member 11 through the base end portion 11b.

As shown in FIGS. 4 to 9, the electric circuit 31 comprises at least one of amplifiers 40 for amplifying echo signals from the ultrasonic transducers 12, switches 41 for switching over between sending the echo signals from the ultrasonic transducers 12 and receiving drive signals for exciting the ultrasonic transducers 12, a multiplexer 42 for selective-switching between the echo signals as well as between the drive signals, an A/D converter 43 for converting the echo signals from an analog form to a digital form, and a D/A converter 44 for converting the drive signals from a digital form to an analog form.

In an embodiment shown in FIG. 4, amplifiers 40 and switches 41 are included in the electric circuit 31, whereas other elements are disposed in the not-shown ultrasound observing device. The switches 41 are, for example, semiconductor switches such as MOSFET, or electromechanical switches that switch their contacts electromechanically, and switch over between sending the echo signals and receiving the drive signals in accordance with switching signals that are sent through the array wiring cable 19 from the ultrasound observing device.

The embodiment shown in FIG. 4 is effective particularly to a case having a relatively small number of ultrasonic transducers 12, like those arranged in the linear array, and the array wiring cable 19 may have a certainly large diameter. Besides, since the amplifiers 40 are included in the electric circuit 31 in FIG. 4, the signals do not suffer from damping or noise that may occur because of transmission loss in the wiring cables. So the echo signals are improved in S/N ratio. Furthermore, because the switches 41 disconnect the signal lines for the drive signals from ones for the echo signals, the amplifiers 40 can be driven at a low voltage, which provides a special effect of saving the part cost and the power consumption.

In an embodiment shown in FIG. 5, not only amplifiers 40 and switches 41 but also a multiplexer 42 are included in the electric circuit 31, and other elements are provided in the ultrasound observing device. The multiplexer 42 selectively switches over between the drive signals or between the echo signals in accordance with a MP (multiplexer) control signal sent through the array wiring cable 19 from the ultrasound observing device.

The embodiment of FIG. 5 is effective particularly to a case having a large number of ultrasonic transducers 12, like those arranged in the two-dimensional array, and the array wiring cable 19 may not be thick. This is because the multiplexer 42 permits reducing the requisite number of signal lines for the drive signals and the echo signals to merely two on the side of the array wiring cable 19, so it is possible to reduce the diameter of the array wiring cable 19. This embodiment is applicable to a case where the number of ultrasonic transducers 12 is relatively small. In that case, the array wiring cable 19 can be made still finer, relieve the stress on the patients.

Figure 6:
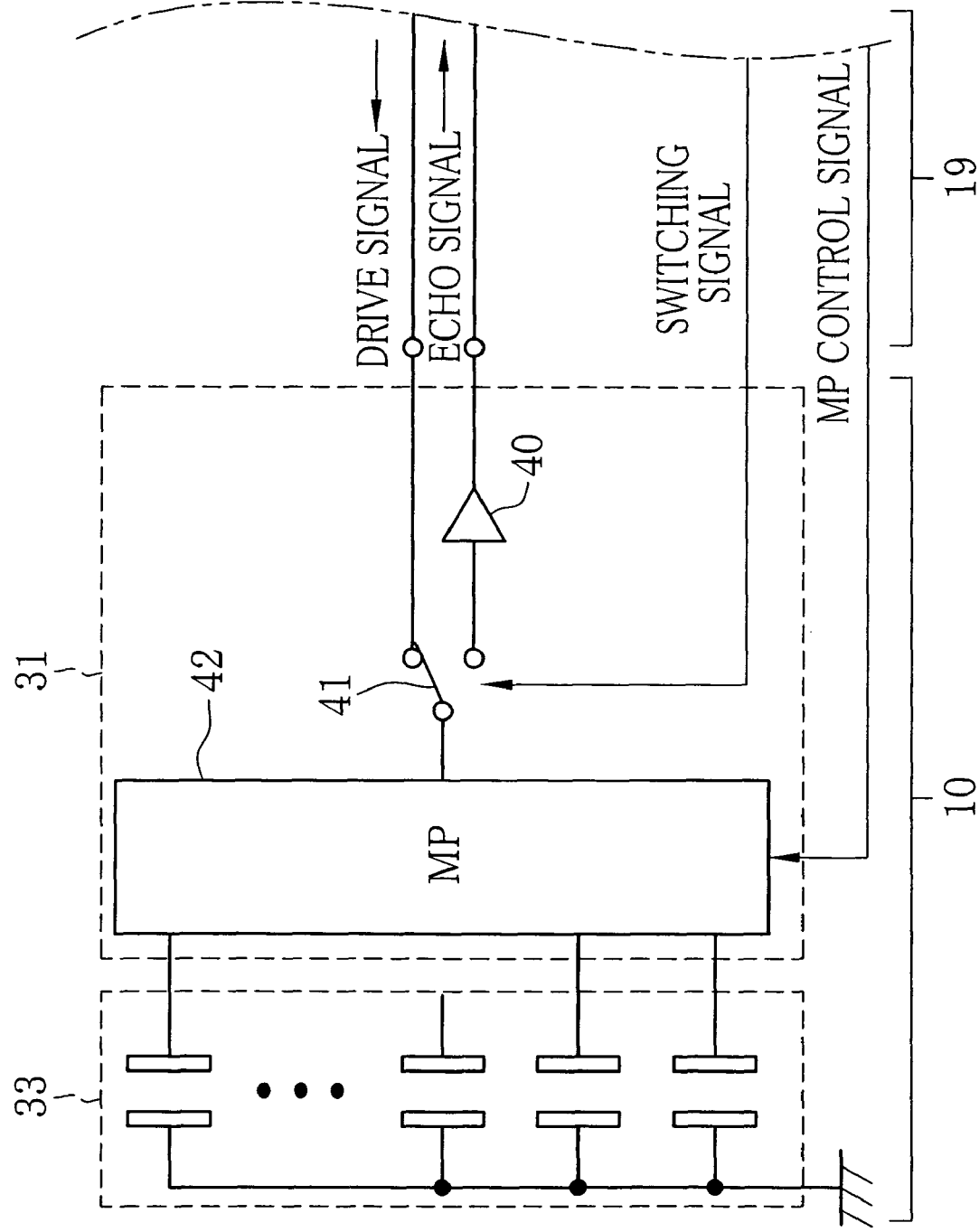
FIG. 6 is a circuit diagram illustrating a still another embodiment wherein an amplifier, a switch and a multiplexer are included in an electric circuit.

FIG. 6 shows another embodiment, wherein the electric circuit 31 includes the same elements as in the embodiment of FIG. 5, but a switch 41 and an amplifier 40 are disposed on the output side of a multiplexer 42. Because this embodiment needs only one amplifier 40 and one switch 41, the parts cost, power consumption and heat generation from the driven elements are reduced. Among all, suppressing heat generation from the tip 2a of the ultrasonic probe 2, a typical example of which is an ultrasonic endoscope, is especially important.

Figure 7:
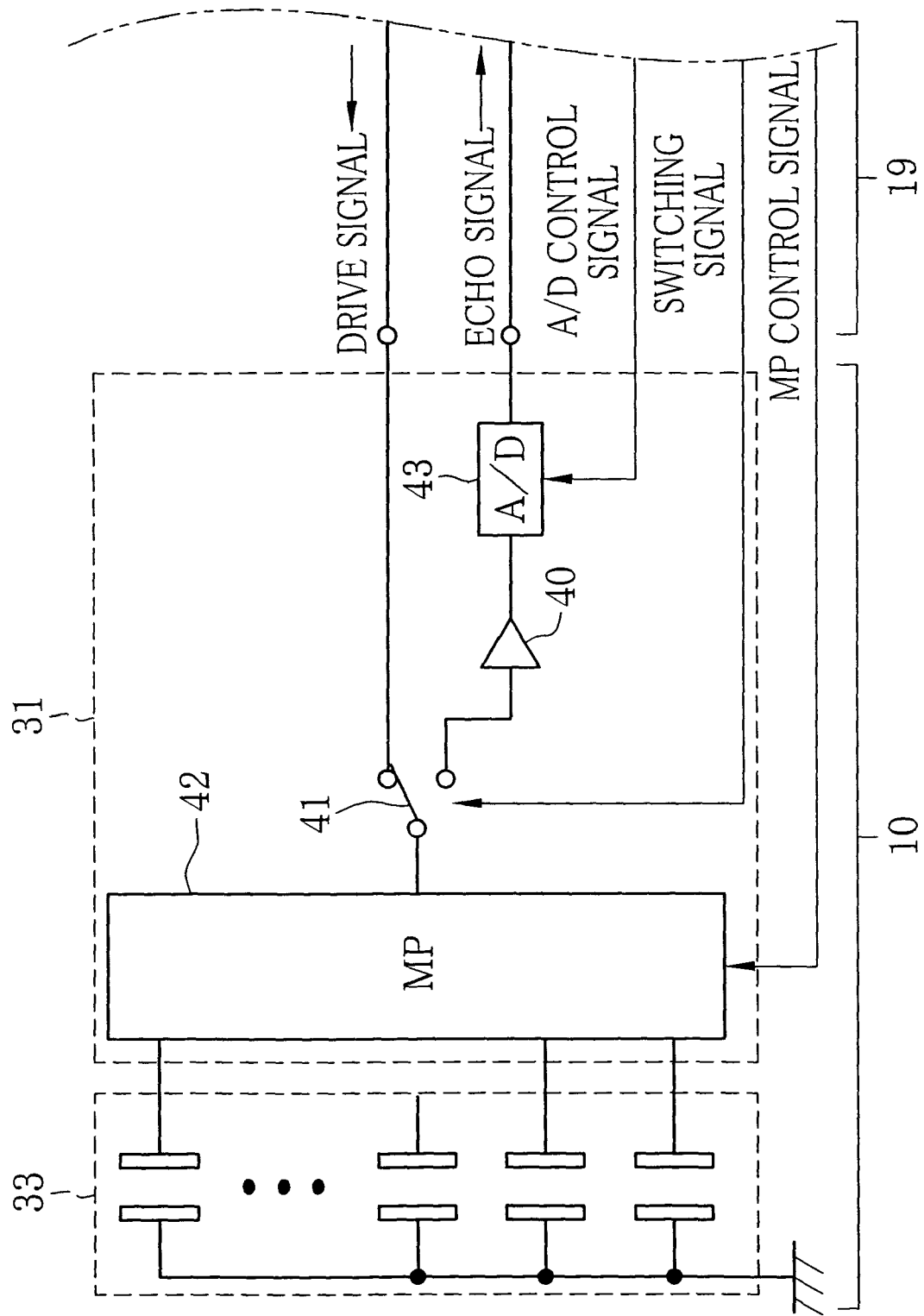
FIG. 7 is a circuit diagram illustrating a further embodiment wherein an amplifier, a switch, a multiplexer and an A/D converter are included in an electric circuit.

In an embodiment shown in FIG. 7, an amplifier 40, a switch 41, a multiplexer 42 and an A/D converter 43 are included in the electric circuit 31, and other elements are provided in the ultrasound observing device. The A/D converter 43 converts the echo signals from analog to digital form in accordance with an A/D control signal sent through the array wiring cable 19 from the ultrasound observing device. In this embodiment, the echo signals are treated as digital signals on the side of the array wiring cable 19, the echo signals will not damp in the array wiring cable 19.

Figure 8:
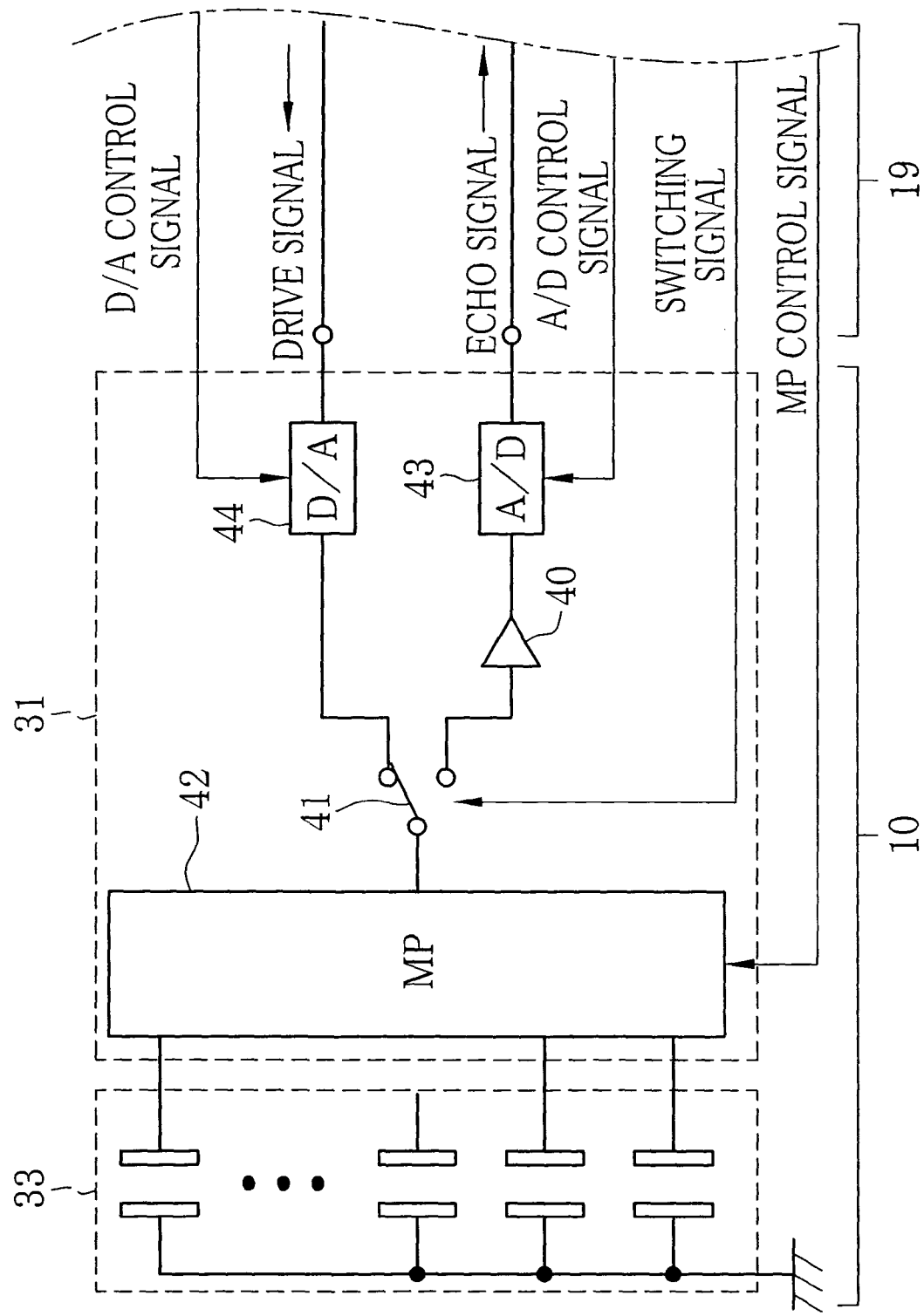
FIG. 8 is a circuit diagram illustrating an embodiment wherein an amplifier, a switch, a multiplexer, an A/D converter and a D/A converter are included in an electric circuit.

In an embodiment shown in FIG. 8, an amplifier 40, a switch 41, a multiplexer 42 and an A/D converter 43 are included in the electric circuit 31, and other elements are provided in the ultrasound observing device. A D/A converter 44 converts the drive signals from digital to analog form in accordance with a D/A control signal sent through the array wiring cable 19 from the ultrasound observing device. In this embodiment, the drive signals are treated as digital signals on the side of the array wiring cable 19, the drive signals will not damp in the array wiring cable 19. Furthermore, because the echo signals are also digitalized through the A/D converter 43, it becomes possible to send the drive signals and the echo signals in the same digital transmission system using optical fibers.

Figure 9:
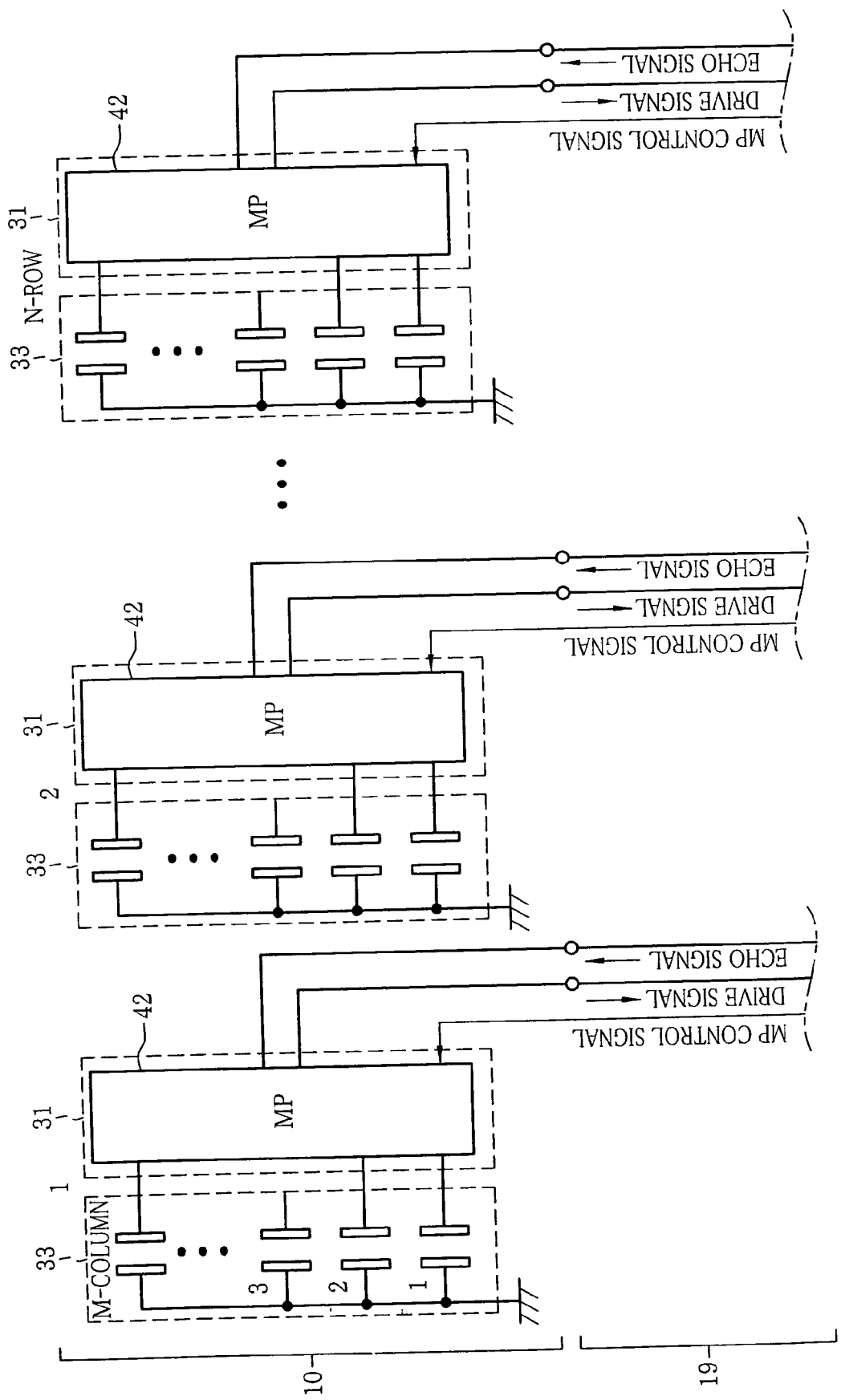
FIG. 9 is a circuit diagram illustrating another embodiment wherein a multiplexer is included in an electric circuit, and is connected individually to each row of an ultrasonic transducer array.

In an embodiment shown in FIG. 9, a multiplexer 42 is disposed on each row of an ultrasonic transducer array 10 consisting of N rows and M columns of ultrasonic transducers, and the multiplexers 42 are included in the electric circuit 31. This embodiment is especially effective to a case where there are a large number of ultrasonic transducers 12, like in a two-dimensional array, or where such a scanning sequence is adopted that the ultrasonic transducers 12 are grouped into several blocks so as to send and receive the drive signals and the echo signals separately block by block. It is to be noted that other appropriate circuits may be included in the electric circuit 31 in addition to the multiplexer 42.

The present invention is not limited to the embodiments shown in FIGS. 4 to 9, but there may be variations in the combinations among the amplifiers 40, the switches 41, the multiplexers 42, the A/D converter 43 and the D/A converter 44. For example, the switches 41 may be omitted in some cases. Where the influence of the noise is negligible, the amplifiers 40 as well as the switches 41 are unnecessary. In order to suppress the noise and reduce the influence of the noise, the signal lines for sending and receiving the drive signals and the echo signals may be gathered with an analog earth line to make a coaxial cable. It is also possible to gather the digital signal lines for the switching signals and the MP control signals and shield them with a digital earth line. Furthermore, it is possible to insert a phase delay circuit in the drive signal line on the side of the ultrasonic transducer array 10. A coil or a filter circuit may be disposed for impedance matching with the array wiring cable 19.

Referring back to FIG. 3, the backing material 32 is formed with through-holes 36 that extend from the electric circuit 31 to the piezoelectric element array 33. Wires 38 for connecting the electric circuit 31 to the piezoelectric element array 33 are put through the through-holes 36. Each wire 38 is soldered to a terminal 37 on the electric circuit 31, and is connected to a pair of electrodes which are not shown but sandwich the piezoelectric element array 33. In order to save the part cost, it is possible serve the backing material 32 as a flexible circuit board, and omit the flexible circuit board 30.

The piezoelectric element array 33 consists of an array of piezoelectric elements 33a arranged linearly or two-dimensionally, and a filling material 33b filled in gaps between the piezoelectric elements 33b. The acoustic impedance matching layer 34 is provided for reducing a difference in acoustic impedance between the piezoelectric elements 33a and the living body. The acoustic lens 35 is made of a silicon resin or the like, and converges ultrasound toward the body part to observe, as the ultrasound is emitted from the ultrasonic transducer array 10. The acoustic lens 35 may be omitted, and a protective layer may be provided instead of the acoustic lens 35.

To take an ultrasonic image of an internal part of a living body, the ultrasonic probe 2 is inserted into the living body, to search the aimed internal part, while observing on the ultrasound observing device optical images as obtained through the imaging device 16. When the tip 2a of the ultrasonic probe 2 reaches the aimed internal part of the body, and a command to capture an ultrasonic image is entered, the switches 41 are activated to switch over sending and receiving of the ultrasonic waves from the ultrasonic transducers 12. Simultaneously, the multiplexer 42 selectively switches between the drive signals and/or the echo signals, as the ultrasonic waves are emitted from the ultrasonic transducer array 10 toward the body part, and then reflected from the body part. The reflected ultrasonic waves are received as the echo signals on the ultrasonic transducer array 10. The echo signals are converted through the ultrasound observing device into an ultrasonic image, which is displayed on a monitor or the like. While observing the optical image or the ultrasonic image, the piercing needle 17 is manipulated to sample the aimed internal body part.

As described so far, the electric circuit 31, including at least some of necessary electric elements for the ultrasonic probe 2, is formed as a layer under the ultrasonic transducers 12, so that the thickness or size of a hard portion, including the ultrasonic transducers 12, is reduced, and thus the load on the patient is relieved. Because the wires 38 that connect the ultrasonic transducers 12 to the electric circuit 31 are put through the through-holes 36 which are formed through the backing material 32, the wires 38 are assembled neatly, saving the mounting cost of the ultrasonic transducers 12.

Because the ultrasonic transducer array 10 is inclined to the intruducing direction D1 of the array wiring cable 19 from the ultrasound observing device, so as to face the base end portion 11b of the back side 11a of the supporting material 11 to the array wiring cable 19, the array wiring cable 19 is smoothly introduced at the base end portion 11b into the supporting member 11, so that it is easy to connect the array wiring cable 19 to the electric circuit 31. This permits making the tip 2a of the ultrasonic probe 2 finer, thereby to lessen the disadvantage of using the wiring cables.

Figure 10:
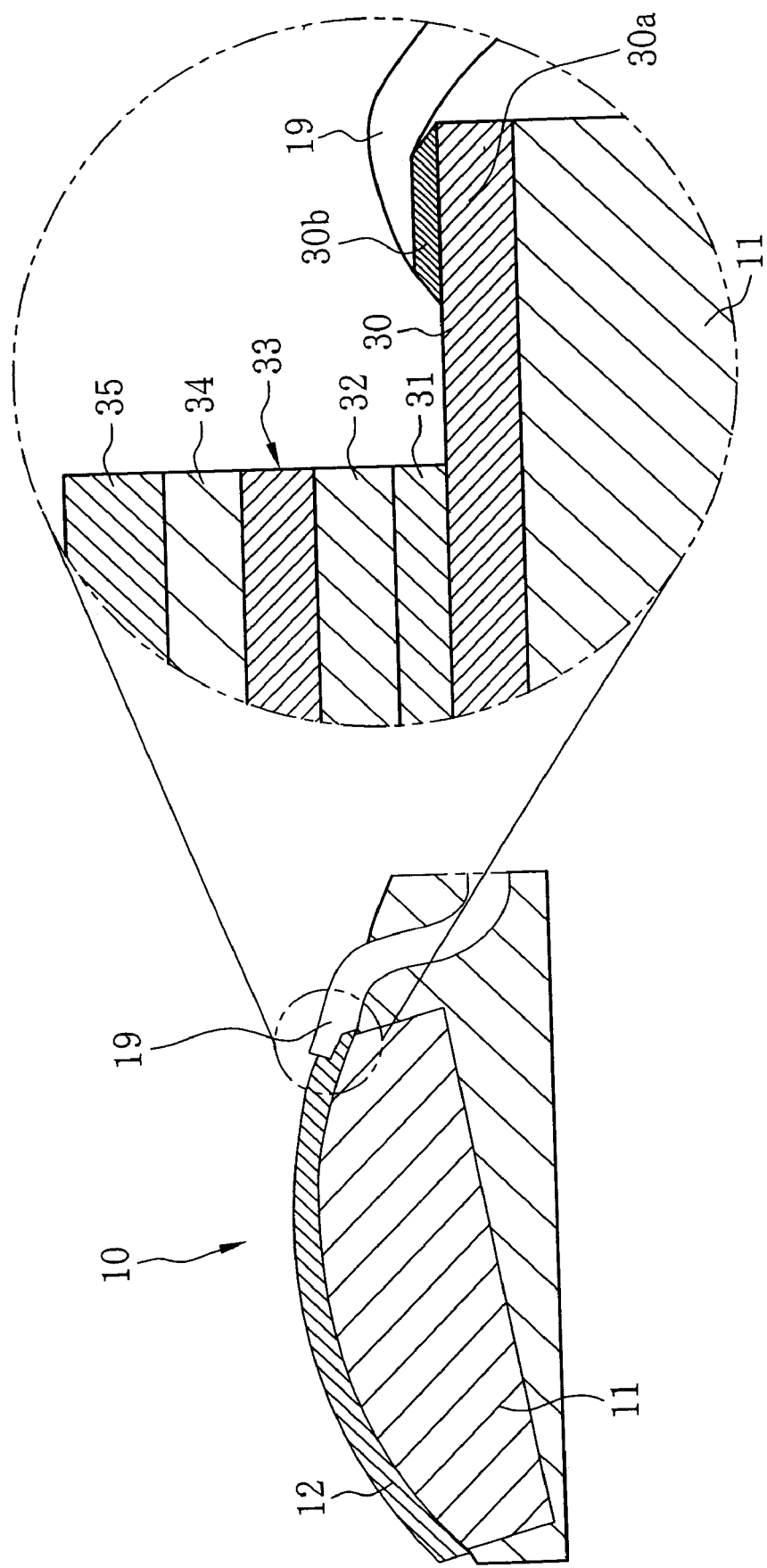
FIG. 10 is a tip of an ultrasonic probe according to another embodiment of the present invention.

The array wiring cable 19 may be connected to the electric circuit 31 in a manner as shown in FIG. 10A, wherein layers 31 to 35 are formed on a flexible circuit board 30 so as to expose an end portion 30a of the flexible circuit board 30, and a terminal 30b is provided on the end portion 30a, so that the array wiring cable 19 is connected electrically to the terminal 30b. This embodiment is also effective for smart wiring.

The present invention has been described with respect to the ultrasonic transducer array 10 constituted of the ultrasonic transducers 12 using the piezoelectric elements 33a, the present invention is applicable to an ultrasonic probe using an ultrasonic transducer array 50 as shown in FIGS. 11 to 14, wherein capacitive micromachined transducers 51a are used as ultrasonic transducers.

Because the capacitive micromachined transducer 51a, hereinafter called simply the capacitive transducer 51a, can be formed integrally on an electric circuit, the wiring can be arranged more smartly as compared to a case using the piezoelectric elements 33a. The capacitive transducer 51a has a wider ultrasonic frequency band than the piezoelectric element 33a, so that it can send and receive the ultrasonic waves of a wider variety of frequencies, enabling ultrasonic diagnosis in a deeper range of the living body. Besides that, the capacitive transducer 51a generates less heat energy than the piezoelectric element 33a, and is superior in efficiency of heat radiation to circumstances, as it can be formed directly on a silicon substrate. Therefore, the capacitive transducer 51a is effective to suppress heat generation, which is one of the most important subjects of the ultrasonic probe for body cavity diagnosis.

Figure 11:
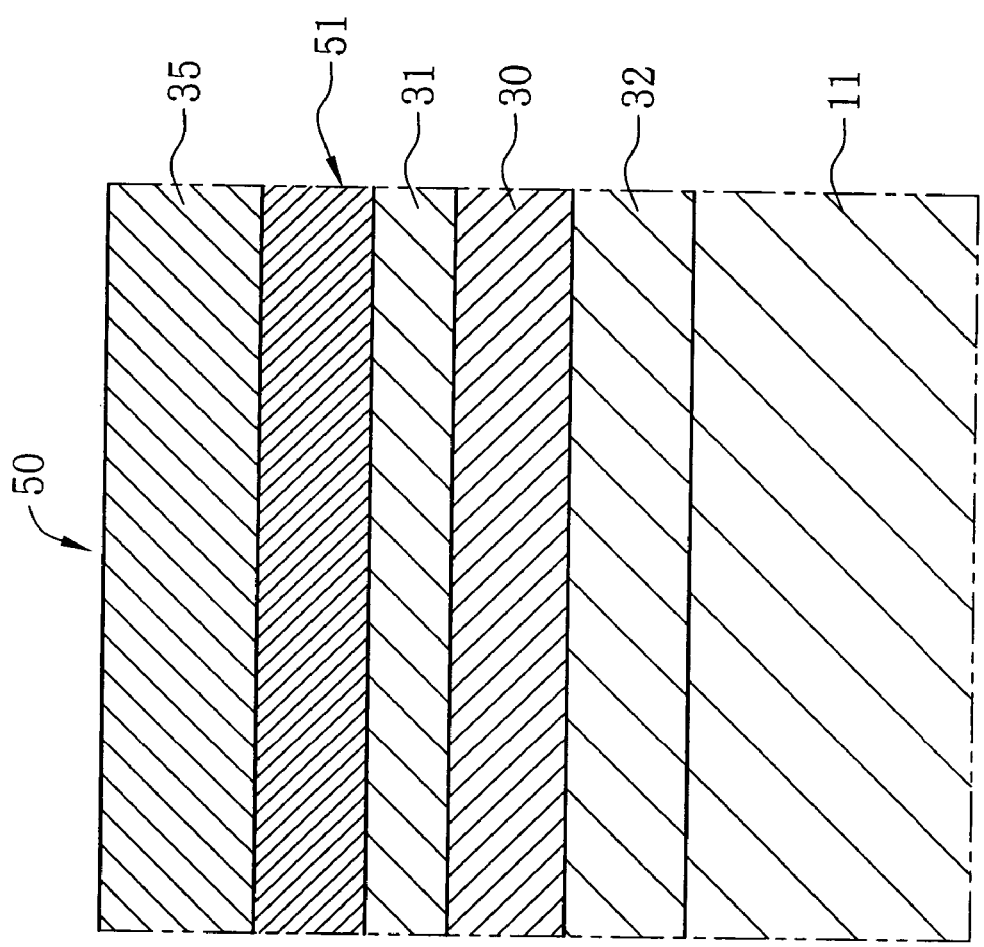
FIG. 11 is an enlarged sectional view of an ultrasonic transducer array using capacitive micromachined ultrasonic transducers.

In FIG. 11, the ultrasonic transducer array 50 has a layered structure wherein a backing material 32, a flexible circuit board 30, an electric circuit 31, a capacitive micromachined ultrasonic transducer array 51, hereinafter called simply the capacitive transducer array 51, and an acoustic lens 35 or a protective layer are formed atop another on a substrate 11. The electric circuit 31 and the capacitive transducer array 51 have a thickness of 20 μm to 30 μm in total, whereas the ultrasonic transducer array 50 as the whole has a thickness of 6 mm to 8 mm.

Figure 12:
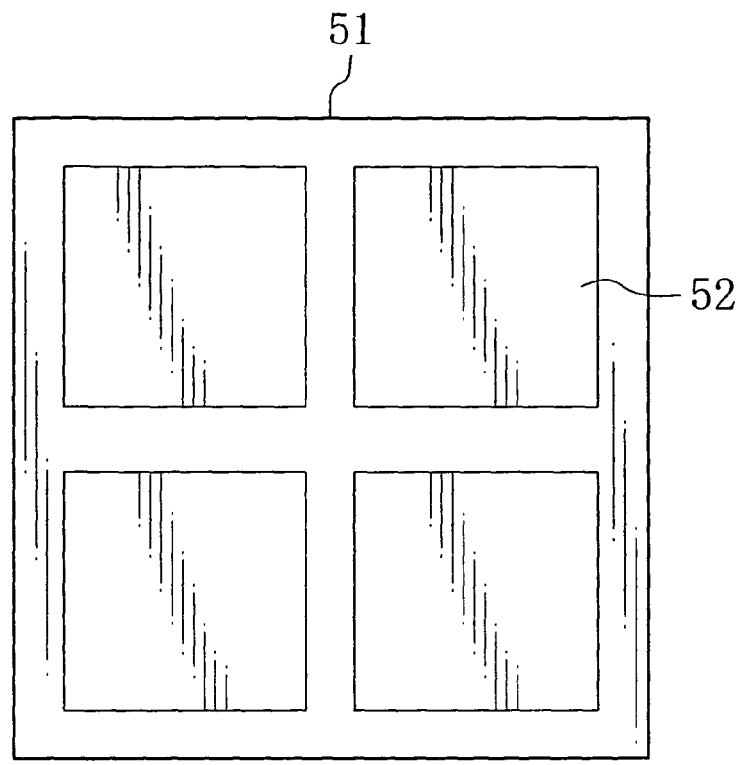
FIG. 12 is a top plan view illustrating an arrangement of the capacitance transducer array.
Figure 13:
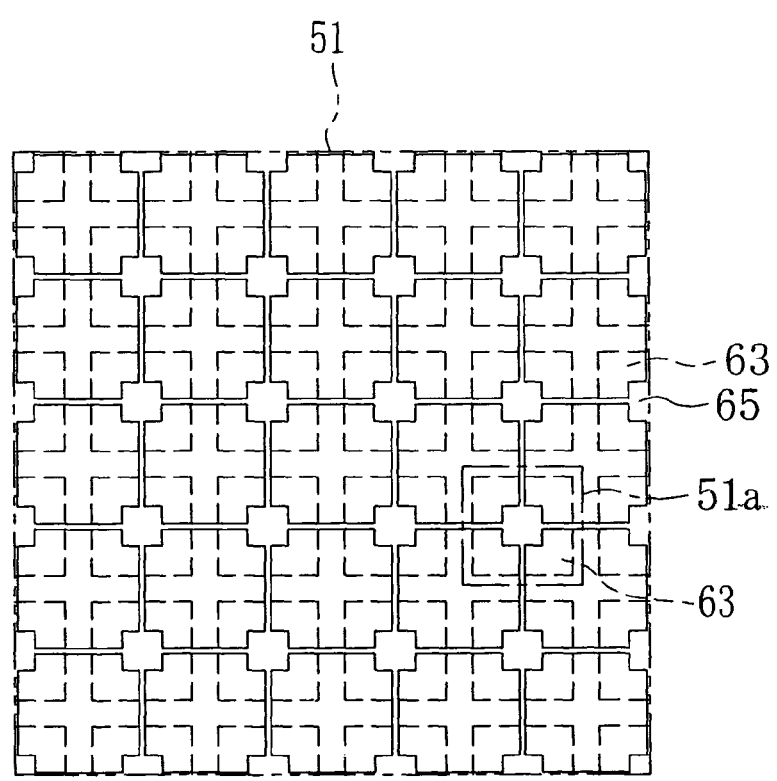
FIG. 13 is an enlarged top plan view of the capacitance transducer array.
Figure 14:
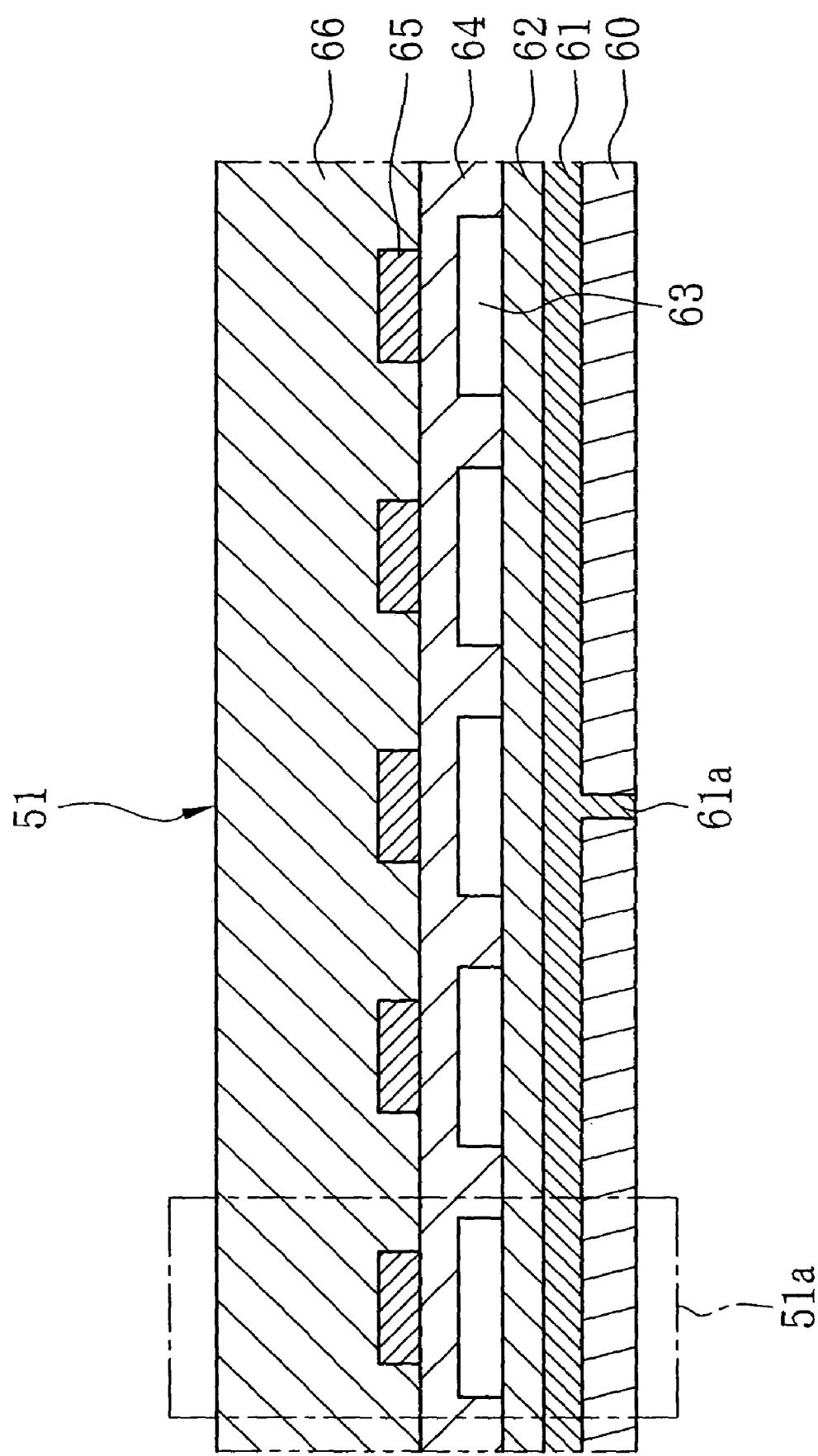
FIG. 14 is an enlarged sectional view of the capacitance transducer array.

As shown in FIG. 12, the capacitive transducer array 51 is sectioned into four segments 52 arranged in 2 rows and 2 columns. Referring to FIGS. 13 and 14 showing an partially enlarged top plane view and a sectional view of the capacitive transducer array 51, the capacitive transducer array 51 is constituted of an insulating layer 60, e.g. $SiO_2$, a bottom electrode 61, e.g. Al, an insulating layer 62, e.g. SiNx, vacuum-sealed gaps 63, a movable insulating layer 64, e.g. SiNx, a top electrode 65, e.g. Al, and a protective insulating layer 66, e.g. $SiO_2$. From the bottom electrode 61 through the insulating layer 60, a terminal 61a extends to connect the electrode 61 electrically to the electric circuit 31. In FIGS. 13 and 14, a portion bounded by a chain-dotted line constitutes the individual capacitance transducer 51a.

Figure 15A:
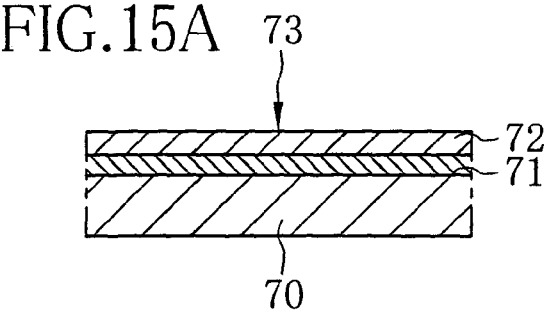
FIGS. 15A to 15H are explanatory diagrams illustrating a sequence of manufacturing the ultrasonic transducer array using the capacitance transducer array.
Figure 15B:
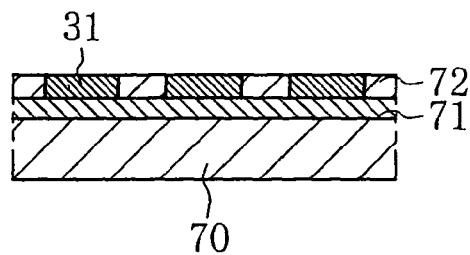

Now a method of manufacturing the ultrasonic transducer array 50 will be concretely described with reference to FIG. 15. First, an SOI (Silicon On Insulator) substrate 73 is provided by forming a silicon layer 72 on an insulating layer 71 of a silicon substrate 70, as shown in FIG. 15A. Then, the electric circuit 31 is formed of semiconductors in the silicon layer 72, as shown in FIG. 15B.

Figure 15C:
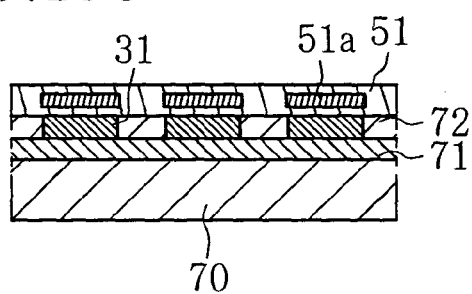
Figure 15D:
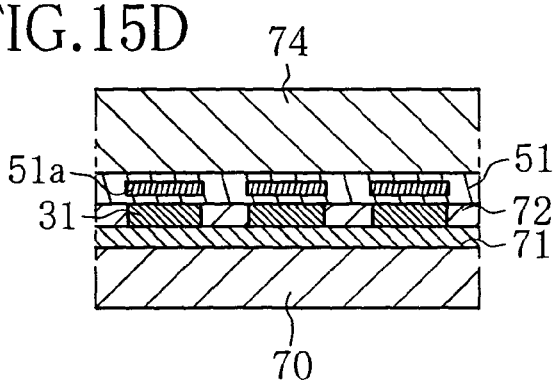
Figure 15E:
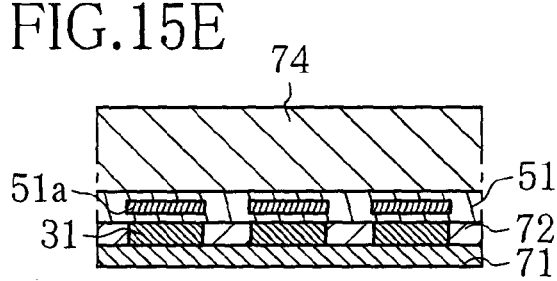
Figure 15F:
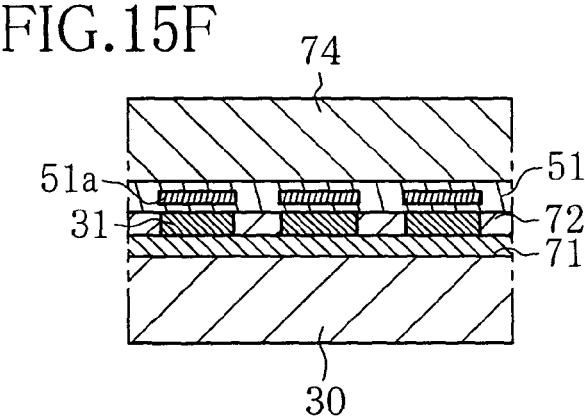
Figure 15G:
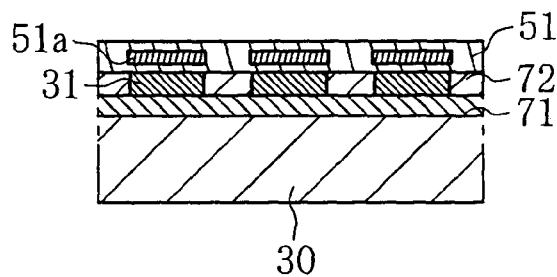

Thereafter, the capacitive transducer array 51 is formed on the electric circuit 31, as shown in FIG. 15C. Then, a temporary supporting member 74 is bonded on the top of the capacitive transducer array 51, as shown in FIG. 15D. Next, the silicon substrate 70 is taken away by electrochemical etching or the like, while leaving the insulating layer 71, as shown in FIG. 15E. After the silicon substrate 70 is removed, the flexible circuit board 30 is put on a back side of the insulating layer 71, as shown in FIG. 15F, and then the temporary supporting member 74 is separated from the capacitive transducer array 51, as shown in FIG. 15G.

Figure 15H:
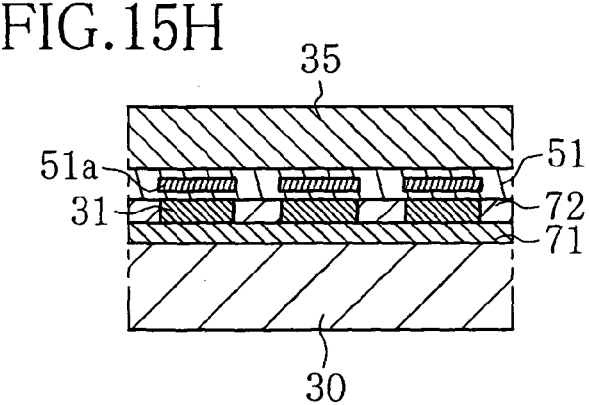

Thereafter, as shown in FIG. 15H, the acoustic lens 35 or the protective layer is joined onto the capacitive transducer array 51. Finally, a sheet having the layered structure of FIG. 15H is put on the supporting member 11, and the wiring for connecting the array wiring cable 19 and other cables is made to complete the ultrasonic probe having the ultrasonic transducer array 50 at its tip. In this way, the ultrasonic probe is manufactured with ease.

It is to be noted that the ultrasonic transducer array 50 may be manufactured in another method insofar as it includes the steps of forming the electric circuit 31 in the silicon substrate, taking the silicon substrate away except but the electric circuit 31, and bonding a flexible substrate on the back side of the electric circuit 31.

Figure 16:
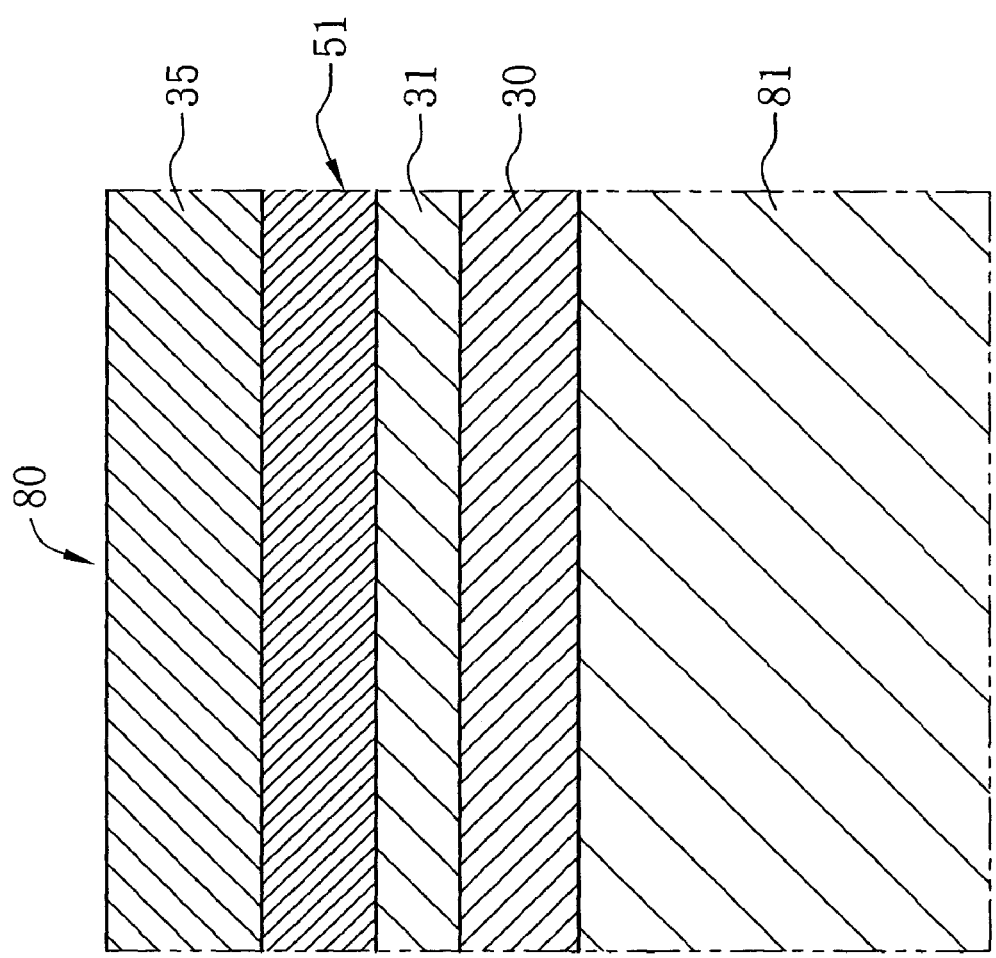
FIG. 16 is an enlarged sectional view of an ultrasonic transducer array using capacitance transducers, according to another embodiment of the present invention.

In place of the supporting member 11 that is made of a rigid material, a supporting member 81 made of an ultrasonic wave absorbing material may be used in an ultrasonic transducer array 80, as shown in FIG. 16. Then, the backing material 32 becomes unnecessary, so it contributes to miniaturizing and economizing the ultrasonic probe.

Figure 17:
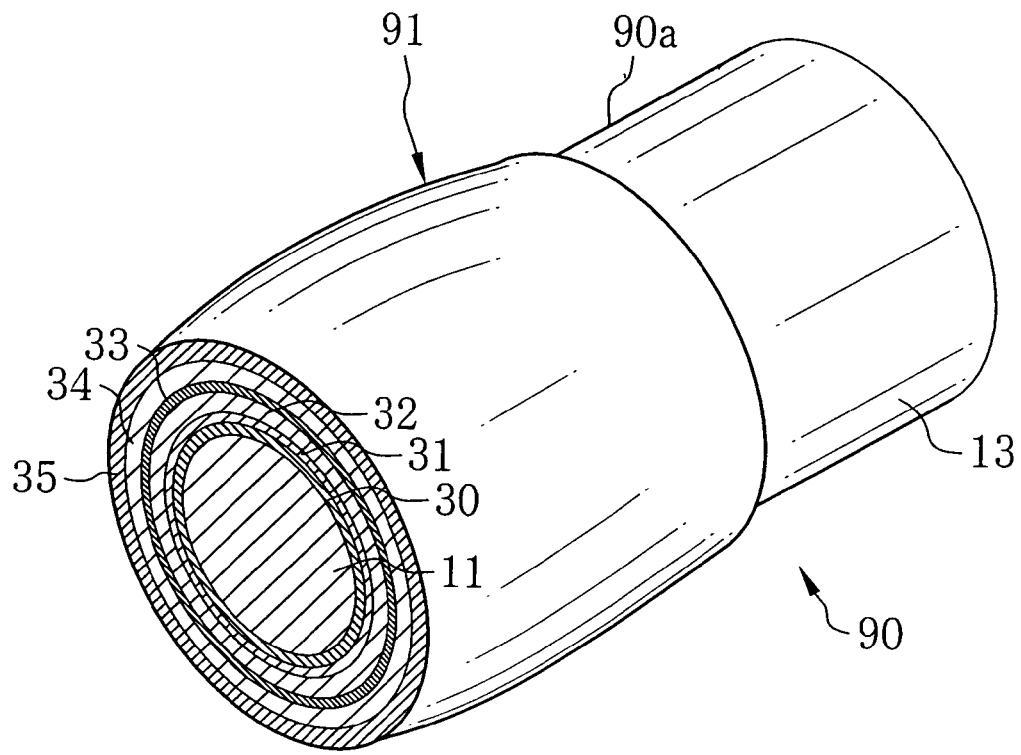
FIG. 17 is a fragmentary sectional view of an ultrasonic probe, with a radial electronic scanning type ultrasonic transducer array using piezoelectric elements.
Figure 18:
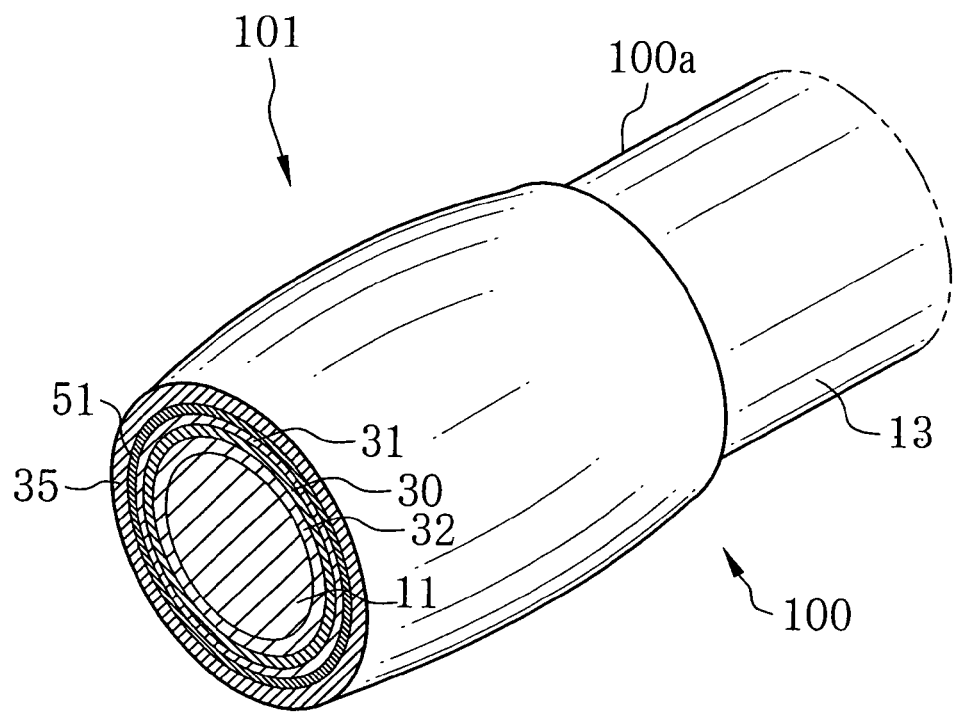
FIG. 18 is a fragmentary sectional view of an ultrasonic probe, with a radial electronic scanning type ultrasonic transducer array using capacitive micromachined ultrasonic transducers.

Although the ultrasonic transducer arrays 10, 50 and 80 of the above embodiments have been described as a convex electronic scanning type, the present invention is applicable to ultrasonic probes using a radial electronic scanning type ultrasonic transducer array, as shown for example in FIGS. 17 and 18. In the radial electronic scanning type, a plurality of ultrasonic transducers are arranged radially by forming respective layers in concentric circles.

Specifically, an ultrasonic transducer array 91 of an ultrasonic probe 90 shown in FIG. 17 uses a piezoelectric element array 33, whereas an ultrasonic transducer array 101 of an ultrasonic probe 100 shown in FIG. 18 uses a capacitive transducer array 51. Although it is not shown in the drawings, an imaging device 16 is mounted in a center portion of a supporting member 11 in each of the ultrasonic transducer arrays 91 and 101. Like the embodiment shown in FIG. 10A, layers 31 to 35 are formed on a flexible circuit board 30 so as to expose an end portion 30a of the flexible circuit board 30, and a terminal 30b is provided on the end portion 30a, so that an array wiring cable 19 is connected electrically to the terminal 30b. Otherwise, the ultrasonic transducer arrays 91 and 101 have the same fundamental structure as the above-described convex electronic scanning type, except that the ultrasonic transducers are arranged radially. Therefore, the equivalent elements are designated by the same reference numerals as used in the above embodiments, and the description of these elements will be omitted.

The present invention is not to be limited to the above embodiment but, on the contrary, various modifications will be possible without departing from the scope of claims appended hereto.

What is claimed is:

1. An ultrasonic probe for intra-cavity diagnosis comprising an ultrasonic transducer array disposed at a tip of said probe, said ultrasonic transducer array comprising a plurality of ultrasonic transducers arranged in an array, and an electric circuit including at least some of necessary electric elements for activating said ultrasonic transducers, said electric circuit being formed as a layer laid under said ultrasonic transducers in a direction where an ultrasonic wave is emitted, wherein said ultrasonic transducers are piezoelectric elements;

wherein said ultrasonic transducer array has a layered structure having at least a flexible substrate, said electric circuit, a backing material, an array of said piezoelectric elements and an acoustic impedance matching layer, which are formed atop another on a rigid supporting member, and wherein said electric circuit and said piezoelectric elements are connected electrically through wires which are disposed in said backing material; and wherein the acoustic impedance matching layer is disposed directly on the array of said piezoelectric elements, the array of said piezoelectric elements is disposed directly on the backing material, the backing material is disposed directly on the electric circuit, and the electric circuit is disposed directly on the flexible substrate.

2. An ultrasonic probe as claimed in claim 1, wherein said flexible substrate is a circuit board having a circuit pattern formed thereon.

3. An ultrasonic probe as claimed in claim 1, wherein said flexible substrate is a circuit board having a circuit pattern formed thereon.

4. An ultrasonic probe as claimed in claim 3, wherein a backing material is provided between said supporting member and said flexible substrate.

5. An ultrasonic probe as claimed in claim 4, further comprising a wiring cable for connecting said electric circuit to an ultrasound observing device that generates drive signals for exiting said ultrasonic transducers and produces ultrasound images from echo signals received from said ultrasonic transducers, said wiring cable being introduced at a base end of a supporting member on which said ultrasonic transducer array is mounted.

6. An ultrasonic probe as claimed in claim 5, wherein ultrasonic transducer array is inclined to an introducing direction of said wiring cable from said ultrasound observing device, such that said base end portion of said supporting material faces said wiring cable.

7. An ultrasonic probe as claimed in claim 4, further comprising a wiring cable for connecting said electric circuit to an ultrasound observing device that generates drive signals for exiting said ultrasonic transducers and produces ultrasound images from echo signals received from said ultrasonic transducers, said wiring cable being connected to a terminal that is provided at an end portion of a flexible substrate that is electrically connected to said electric circuit.

8. An ultrasonic probe as claimed in claim 1, wherein said ultrasonic probe is mounted with an imaging device comprising an objective optical system for forming an optical image of an internal body part to investigate, and imaging elements for taking said optical image to output image signals.

9. The ultrasonic probe according to claim 1, wherein the electric circuit in its entirety is laid under said ultrasonic transducers.

10. The ultrasonic probe according to claim 1, wherein the array in which the plurality of ultrasonic transducers is arranged is a rectangular array.

11. The ultrasonic probe according to claim 1, wherein said ultrasonic transducer array is of a convex electronic scanning type and wherein said ultrasonic transducer array is inclined toward the tip of the probe.

12. An ultrasonic probe as claimed in claim 1, wherein said supporting member has an ultrasound absorbing function.

13. An ultrasonic probe as claimed in claim 1, wherein said electric circuit comprises at least one of amplifiers for amplifying echo signals from said ultrasonic transducers, switches for switching over between sending said echo signals from said ultrasonic transducers and receiving drive signals for exciting said ultrasonic transducers, a multiplexer for selective-switching between said echo signals and/or between said drive signals, an A/D converter for analog-to-digital conversion of said echo signals, and a D/A converter for digital-to-analog conversion of said drive signals.

14. An ultrasonic probe as claimed in claim 1, wherein said ultrasonic transducer array is of a radial electronic scanning type wherein said ultrasonic transducers are arranged radially in a concentric circle.

15. An ultrasonic probe as claimed in claim 14, further comprising a wiring cable for connecting said electric circuit to an ultrasound observing device that generates drive signals for exiting said ultrasonic transducers and produces ultrasound images from echo signals received from said ultrasonic transducers, said wiring cable being connected to a terminal that is provided at an end portion of a flexible substrate that is electrically connected to said electric circuit.

* * * * *